United States Patent [19]

Browne

[11] Patent Number: 4,588,732

[45] Date of Patent: May 13, 1986

[54] CERTAIN IMIDAZO(1,5-A)PYRIDINE DERIVATIVES AND THEIR USE AS THROMBOXANE SYNTHETASE INHIBITORS

[75] Inventor: Leslie J. Browne, Morris Plains, N.J.

[73] Assignee: Ciba-Geigy Corporation, Ardsley, N.Y.

[21] Appl. No.: 451,902

[22] Filed: Dec. 21, 1982

[51] Int. Cl.[4] ............... A61K 31/44; C07D 471/04
[52] U.S. Cl. ................. 514/300; 546/121
[58] Field of Search .............. 546/121; 424/256

[56] References Cited

U.S. PATENT DOCUMENTS

| | | | |
|---|---|---|---|
| 3,790,586 | 2/1974 | Irikura et al. | 546/121 |
| 4,226,878 | 10/1980 | Iizuka et al. | 424/273 R |
| 4,256,757 | 3/1981 | Hayashi et al. | 424/273 R |
| 4,361,567 | 11/1982 | Bristol | 424/256 |
| 4,409,226 | 10/1983 | Bristol et al. | 546/121 |
| 4,444,775 | 4/1984 | Ford | 546/121 |
| 4,470,986 | 9/1984 | Browne | 546/121 |

FOREIGN PATENT DOCUMENTS

| | | |
|---|---|---|
| 15171 | 9/1980 | European Pat. Off. |
| 68386 | 1/1983 | European Pat. Off. |
| 2016452 | 9/1979 | United Kingdom. |
| 2038821 | 7/1980 | United Kingdom. |

OTHER PUBLICATIONS

P. Blatcher et al., Tetrahedron Letters 21, 2195 (1980).
G. J. Durant et al., J. Medicinal Chemistry 16, 1972 (1973).
W. W. Paudler et al., J. Heterocyclic Chemistry 3, 33 (1966).
O. Fuentes et al., J. Org. Chemistry 40, 1210 (1975).

*Primary Examiner*—Henry R. Jiles
*Assistant Examiner*—Bernard I. Dentz
*Attorney, Agent, or Firm*—Norbert Gruenfeld

[57] ABSTRACT

Disclosed are compounds of the formula I

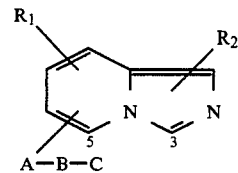

or a 5,6,7,8-tetrahydro derivative thereof, wherein $R_1$ is hydrogen, halogen, lower alkyl, lower alkoxy, hydroxy, or aryl-lower alkoxy in which aryl represents phenyl or phenyl substituted by lower alkoxy, lower alkyl, halogen or trifluoromethyl; $R_2$ represents hydrogen, halogen, or lower alkyl; C represents carboxy, lower alkoxycarbonyl, unsubstituted or mono- or di-(lower alkyl) substituted carbamoyl, cyano, formyl, hydroxymethyl, 5-tetrazolyl, dihydro-2-oxazolyl, dihydro-2-oxazolyl substituted by lower alkyl, or hydroxycarbamoyl; and (a) A represents ethenylene or ethenylene substituted by lower alkyl; B is straight chain or branched alkylene of 1 to 12 carbon atoms, alkynylene or alkenylene of 2 to 12 carbon atoms, phenylene-lower alkylene, phenylene-lower alkenylene, phenylene, or phenylene-(thio or oxy)-lower alkylene; or (b) A represents a direct bond; B represents lower alkylenephenylene, phenylene lower alkylene, phenylene, lower alkylene-(thio or oxy)-lower alkylene, lower alkylene-(thio or oxy)-phenylene, phenylene-(thio or oxy)-lower alkylene, phenylene-lower alkenylene, lower alkylenephenylene-lower alkenylene, or straight chain or branched alkadienylene of 5 to 12 carbon atoms; or a pharmaceutically acceptable salt thereof; and methods of synthesis thereof. Said compounds are useful as selective thromboxane synthetase inhibitors for the treatment of diseases such as cerebral ischaemia, shock, thrombosis and ischaemic heart disease.

21 Claims, No Drawings

CERTAIN IMIDAZO(1,5-A)PYRIDINE DERIVATIVES AND THEIR USE AS THROMBOXANE SYNTHETASE INHIBITORS

SUMMARY OF THE INVENTION

The present invention is concerned with imidazo[1,5-a]pyridine derivatives representing potent and highly specific thromboxane synthetase inhibitors.

The foregoing advantages and attributes render the imidazo[1,5-a]pyridine derivatives of this invention particularly useful when administered, alone or in combination, to mammals, e.g. for the treatment or prevention of diseases responsive to the inhibition of thromboxane synthetase comprising cardiovascular disorders such as thrombosis, atherosclerosis, cerebral ischaemic attacks, myocardial infarction, angina pectoris, hypertension; respiratory disorders, such as asthma; inflammatory disorders; carcinoma, such as tumor metastasis; and migraine headache.

This invention thus relates to imidazo[1,5-a]pyridine derivatives useful as selective thromboxane synthetase inhibitors, processes for preparing same, pharmaceutical compositions comprising said compounds, and methods of treating diseases responsive to inhibition of thromboxane synthetase by administration of said compounds and compositions to mammals.

Particularly the invention relates to imidazo[1,5-a]pyridine derivatives of formula I

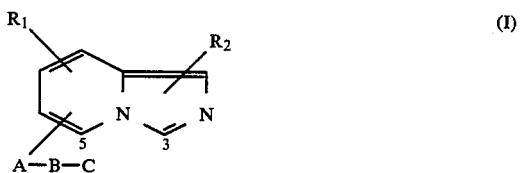

or 5,6,7,8-tetrahydro derivatives thereof, wherein $R_1$ is hydrogen, halogen, lower alkyl, lower alkoxy, hydroxy, or aryl-lower alkoxy in which aryl represents phenyl or phenyl mono- or di-substituted by lower alkoxy, lower alkyl, halogen or trifluoromethyl; $R_2$ represents hydrogen, halogen, or lower alkyl; C represents carboxy, lower alkoxycarbonyl, unsubstituted or mono- or di-(lower alkyl) substituted carbamoyl, cyano, formyl, hydroxymethyl, 5-tetrazolyl, 4,5-dihydro-2-oxazolyl, 4,5-dihydro-2-oxazolyl substituted by lower alkyl, or hydroxycarbamoyl; and (a) A represents ethenylene (vinylene) or ethenylene (vinylene) substituted by lower alkyl, and B is straight chain or branched alkylene of 1 to 12 carbon atoms, alkynylene or alkenylene of 2 to 12 carbon atoms each, phenylene-lower alkylene, phenylene-lower alkenylene, phenylene, phenylene-(thio or oxy)-lower alkylene; or (b) A represents a direct bond and B represents lower alkylenephenylene, phenylene lower alkylene, phenylene, lower alkylene-(thio or oxy)-lower alkylene, lower alkylene-(thio or oxy)-phenylene, phenylene-(thio or oxy)-lower alkylene, phenylene lower alkenylene, lower alkylenephenylene lower alkenylene, or straight chain or branched alkadienylene of 5 to 12 carbon atoms; and pharmaceutically acceptable salts thereof.

Preferred are the compounds of formula I wherein the group —A—B—C is attached at the 5-position.

One embodiment of the invention is represented by compounds of formula I wherein $R_1$ is hydrogen, halogen, lower alkyl, lower alkoxy, hydroxy, phenyl-lower alkoxy, or phenyl-lower alkoxy mono- or di-substituted on the phenyl ring by lower alkoxy, lower alkyl or halogen; $R_2$ represents hydrogen, halogen or lower alkyl; A represents ethenylene or ethenylene substituted by lower alkyl; B is a straight chain or branched alkylene of 1 to 12 carbon atoms, alkynylene or alkenylene of 2 to 12 carbon atoms each, phenylene-lower alkylene, phenylene-lower alkenylene, phenylene, phenylene (thio or oxy)-lower alkylene; C represents carboxy, lower alkoxycarbonyl, unsubstituted or mono- or di(-lower alkyl) substituted carbamoyl, cyano, hydroxymethyl, formyl, 5-tetrazolyl, 4,5-dihydro-2-oxazolyl, 4,5-dihydro-2-oxazolyl substituted by lower alkyl, or hydroxycarbamoyl; and pharmaceutically acceptable salts thereof.

Preferred are said compounds of formula I wherein A represents ethenylene; B represents straight chain or branched alkylene of 1 to 12 carbon atoms, alkenylene of 2 to 12 carbon atoms, phenylene, phenylene-oxy-lower alkylene; $R_1$, $R_2$ and C are as defined above; and pharmaceutically acceptable salts thereof.

Preferred in turn are said compounds of formula I wherein A represents ethenylene; B represents straight chain or branched alkylene or alkenylene of 2 to 6 carbon atoms each, phenylene or phenylene-oxy-alkylene of 7 to 11 carton atoms; $R_1$ and $R_2$ are hydrogen and C represents carboxy or lower alkoxycarbonyl; and the group —A—B—C is attached at a 5-position of the imidazo[1,5-a]pyridine nucleus.

Particularly preferred are the compounds of formula II

wherein B represents straight chain or branched alkylene or alkenylene each of 2 to 4 carbon atoms; C represents carboxy or lower alkoxy carbonyl; and pharmaceutically acceptable salts thereof.

Another embodiment of the invention is represented by compounds of formula I or 5,6,7,8-tetrahydro derivatives thereof, wherein $R_1$ is hydrogen, halogen, lower alkyl, lower alkoxy, hydroxy or aryl-lower alkoxy in which aryl represents phenyl or phenyl mono- or di-substituted by lower alkoxy, lower alkyl, halogen or trifluoromethyl; $R_2$ represents hydrogen, halogen or lower alkyl; C represents carboxy, lower alkoxycarbonyl, unsubstituted or mono- or di-(lower alkyl) substituted carbamoyl, cyano, hydroxymethyl, formyl, 5-tetrazolyl, 4,5-dihydro-2-oxazolyl, 4,5-dihydro-2-oxazolyl substituted by lower alkyl, or hydroxycarbamoyl; A represents a direct bond; and B represents lower alkylenephenyl lower alkylene, lower alkylenephenylene, phenylene lower alkylene, phenylene, lower alkylene-(thio or oxy)-lower alkylene, lower alkylene-(thio or oxy)-phenylene, phenylene-(thio or oxy)-lower alkylene, phenylene lower alkenylene, lower alkylenephenylene lower alkenylene, or straight chain or branched alkadienylene of 5 to 12 carbon atoms; or pharmaceutically acceptable salts thereof.

Preferred are said compounds of formula I wherein A represents a direct bond; B represents phenylene, (alkylenephenylene, phenylenealkylene, alkylenethiophenylene, alkyleneoxyphenylene) of 7 to 10 carbon atoms, or lower alkylene-(thio or oxy)-lower alkylene of 4 to 10 carbon atoms, or phenylene-lower alkenylene of 8 to 10 carbon atoms; C represents carboxy, lower alkoxycarbonyl, carbamoyl, hydroxycarbamoyl, 5-tetrazolyl or hydroxymethyl; $R_1$ and $R_2$ are hydrogen; or pharmaceutically acceptable salts thereof.

Further preferred are last said compounds of formula I wherein B represents lower alkylene-(thio- or oxy)-lower alkylene of 4 to 10 carbon atoms, phenylene, or phenylene-lower alkenylene of 8 to 10 carbon atoms; and A, C, $R_1$ and $R_2$ have meaning as described above.

Preferred in turn are all of the above said compounds of formula I wherein the said group B—C is directly attached at the 5-position of the imidazo[1,5-a]pyridine nucleus.

Particularly preferred are the compounds of formula III

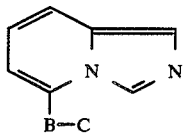

(III)

wherein B represents lower alkylene-(thio- or oxy)-lower alkylene of 4 to 10 carbon atoms, phenylene, phenylene-lower alkylene or lower alkylene phenylene of 7 to 10 carbon atoms each, alkylenethiophenylene or alkyleneoxyphenylene of 7 to 10 carbon atoms each, or phenylene-lower alkenylene of 8 to 10 carbon atoms; C represents carboxy, lower alkoxycarbonyl or carbamoyl; and pharmaceutically acceptable salts thereof.

The general definitions used herein have the following meanings within the scope of the present invention.

A "straight chain or branched alkylene" represents $C_{1-12}$ alkylene preferably propylene, butylene, pentylene or hexylene, said radicals being unsubstituted or substituted by one or more lower alkyl groups with the proviso that the total number of carbon atoms equals no more than 12.

The term "straight chain or branched alkenylene" represents $C_{2-12}$ alkenylene preferably ethenylene (vinylene), propenylene, 1- or 2-butenylene, 1- or 2-pentenylene, 1-, 2- or 3-hexenylene, said radicals being unsubstituted or substituted by one or more lower alkyl groups with the proviso that the total number of carbon atoms equals no more than 12.

The term "straight chain or branched alkynylene" represents $C_{2-12}$ alkynylene preferably ethynylene, propynylene, 1- or 2-butynylene, 1- or 2-pentynylene, 1-, 2- or 3-hexynylene, said radicals being unsubstituted or substituted by one or more lower alkyl groups with the proviso that the total number of carbon atoms equals no more than 12.

A "straight chain or branched alkadienylene represents $C_5C_{12}$ alkadienylene, preferably lower alkylenebutadienylene containing 1 to 7 carbon atoms, advantageously 2 to 5 carbon atoms in the alkylene portion.

The term "lower" referred to above and hereinafter in connection with organic radicals or compounds respectively defines such with up to and including 7, preferably up to and including 4 and advantageously one or two carbon atoms.

A lower alkyl group preferably contains 1-4 carbon atoms and represents for example ethyl, propyl, butyl or advantageously methyl.

A lower alkoxycarbonyl group preferably contains 1-4 carbon atoms in the alkoxy portion and represents for example methoxycarbonyl, propoxycarbonyl, isopropoxycarbonyl or advantageously ethoxycarbonyl. A mono-(lower alkyl)carbamoyl group preferably contains 1-4 carbon atoms in the alkyl portion and is for example N-methylcarbamoyl, N-propylcarbamoyl or advantageously N-ethylcarbamoyl. A di-(lower alkyl)carbamoyl group preferably contains 1-4 carbon atoms in each lower alkyl portion and represents for example N,N-dimethylcarbamoyl, N-methyl-N-ethylcarbamoyl and advantageously N,N-diethylcarbamoyl.

Phenylene represents o-, m-, and preferably p-phenylene.

A lower alkylenephenylene group, a phenylene-lower-alkylene group, a lower alkylenephenylene-lower-alkylene group, a lower alkylene-(thio or oxy)-phenylene group, a phenylene-(thio or oxy)-lower alkylene group, a phenylene-lower-alkenylene group or a lower alkylenephenylene-lower-alkenylene group preferably contains 1 to 4 carbon atoms in each alkylene or 2 to 4 carbon atoms in each alkenylene portion. The lower alkylene and alkenylene portions may be straight chain or branched.

A lower alkylene-(thio or oxy)-lower alkylene group is straight chain or branched and may contain a total of 2 to 12 carbon atoms, preferably 4 to 10 carbon atoms, advantageously 3 to 6 carbon atoms.

An aryl group such as in aryl-lower alkoxy represents preferably phenyl or phenyl mono- or di-substituted by lower alkyl, halogen or lower alkoxy.

An aryl lower alkoxy group advantageously represents benzyloxy.

A lower alkoxy group preferably contains 1-4 carbon atoms and represents for example, ethoxy, propoxy or advantageously methoxy.

Halogen is preferably fluorine and chlorine, but may also represent bromine or iodine.

Pharmaceutically acceptable salts are preferably metal or ammonium salts of said compounds of formula I when C represents carboxy, 5-tetrazolyl or hydroxycarbamoyl, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine, dicyclohexylamine, triethanolamine, ethylenediamine, tris-(hydroxymethyl)-aminomethane or benzyl-trimethylammonium hydroxide. The compounds of Formula I form acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively inhibiting the release of thromboxane through selective inhibition of thromboxane synthetase in mammals. The compounds are thus useful for treating diseases responsive to thromboxane synthetase inhibition in mammals including man.

These effects are demonstrable in vitro assay tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 and 100 mg/kg/day, preferably between about 0.10 and 50 mg/kg/day, advantageously between about 1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}$C-arachidonic acid is incubated with an enzyme preparation consisting of solubilized and partially purified prostaglandin cyclo-oxygenase from sheep seminal vesicles and a crude microsomal preparation of thromboxane synthetase from lysed hyman platelets. The test compound (dissolved in buffer, or if necessary, in a small amount of ethanol) is added to the incubation medium. At the end of the incubation period (30 minutes), Prostaglandin $E_2$ (PGE$_2$) is reduced to a mixture of Prostaglandin $F_2\alpha$ and $F_2\beta$ (PGF$_2\alpha + \beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene:acetone:glacial acetic acid (100 volumes:100 volumes:3 volumes). The radioactive zones are located; those corresponding to Thromboxane $B_2$ (TxB$_2$) and PGF$_2\alpha + \beta$ are transferred to liquid scintillation vials and counted. The ratio of counts for TxB$_2$/PGF$_2\alpha + \beta$ is calculated for each concentration of test compound and IC$_{50}$ values are determined graphically as the concentration of test compound at which the ratio of TxB$_2$/PGF$_2\alpha + \beta$ is reduced to 50% of the control value.

The in-vitro effect on prostaglandin cyclooxygenase is measured by a modification of the method of Takeguchi et al described in Biochemistry 10, 2372 (1971); the testing procedure is as follows:

Lyophilized sheep seminal vesicle microsomes are utilized as the prostaglandin-synthesizing enzyme preparation. The conversion of $^{14}$C-arachidonic acid to PGE$_2$ is measured. Test compounds (dissolved in buffer, or if necessary, in small amount of ethanol) are added to the incubation mixture. The prostaglandins are extracted and separated by thin-layer chromatography; the plates are scanned, the radioactive zones corresponding to PGE$_2$ are transferred to liquid scintillation vials and counted for radioactivity. IC$_{50}$ values for inhibition are determined graphically as the concentration of test compound causing a 50% reduction in the amount of PGE$_2$ synthesized.

The in-vitro effect on prostacyclin (PGI$_2$) synthetase is measured analogous to the method of Sun et al., Prostaglandins 14, 1055 (1977);

The testing procedure is as follows:

$^{14}$C-Arachidonic acid is incubated with an enzyme mixture consisting of solubilized and partially purified prostaglandin cyclo-oxygenase from sheep seminal vesicles and crude PGI$_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-PGF$_1\alpha$ (a stable end product of prostacyclin biotrasformation) and PGE$_2$ are transferred to liquid scintillation vials and counted. The ratio of counts for 6-keto-PGF$_1\alpha$/PGE$_2$ is calculated for each concentration of test compound used. IC$_{50}$ values for inhibition are determined graphically as the concentration of test compound at which the ratio of 6-keto-PGF$_1\alpha$/PGE$_2$ is reduced to 50% of the control.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane $B_2$ and another aliquot for 6-keto-PGF$_1\alpha$, the stable metabolites of thromboxane $A_2$ and prostacyclin (PGI$_2$) respectively, by radioimmunoassay.

Compounds of the formula I are potent and selective, thromboxane synthetase inhibitors. At and above the effective dose levels for thromboxane synthetase inhibition neither the beneficial prostacyclin synthetase enzyme system nor the prostaglandin cyclooxygenase enzyme system is significantly inhibited. Surprisingly, the prostacyclin levels are significantly increased.

Illustrative of the invention, e.g. 5-[p-(2-carboxyprop-1-enyl)phenyl]imidazo[1,5-a]pyridine has an IC$_{50}$ of about $1 \times 10^{-7}$M for thromboxane synthetase inhibition. Said compound reduces the plasma concentration of thromboxane $B_2$ by over 50% at an oral dose of 5 mg/Kg or lower in the rat. A significant increase in the plasma level of the prostacyclin metabolite 6-keto-PGF$_1\alpha$ is observed at similar doses.

Further illustrative of the invention, e.g. 5-(4-carboxybuta-1,3-dienyl)imidazo[1,5-a]pyridine has an IC$_{50}$ of about $3 \times 10^{-8}$M for thromboxane synthetase inhibition. Said compound reduces the plasma concentration of thromboxane $B_2$ by over 50% in the rat at an oral dose of 5 mg/Kg p.o. or lower. a significant increase in the plasma level of the prostacyclin metabolite 6-keto-PGF$_1$-$\alpha$ is also observed.

The aforementioned advantageous properties render the compounds of this invention of great value as specific therapeutic agents for mammals e.g. for the treatment of cardiovascular diseases such as thromboembolism.

The compounds of the invention may be prepared by
(a) cyclizing a compound of the formula

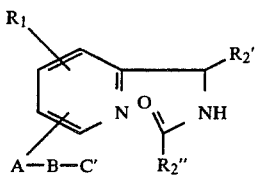

wherein $R_2'$, and $R_2''$ represent hydrogen or lower alkyl; $R_1$, A and B have meaning given above; and C' represents carboxy, lower alkoxycarbonyl, unsubstituted or mono-or di-(lower alkyl) substituted carbamoyl, cyano, hydroxymethyl, lower alkanoyloxymethyl, etherified hydroxymethyl, halomethyl, 5-tetrazolyl, 4,5-dihydro-2-oxazolyl, 4,5-dihydro-2-oxazolyl substituted by lower alkyl, hydroxycarbamoyl, halo, lower alkylenedioxymethyl; to yield a compound of formula Ia

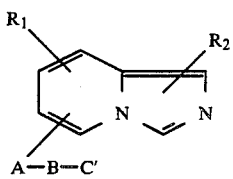

converting any resulting compound wherein C' differs from C into a compound of formula I; and if desired converting any resulting compound of formula I into another compound of the invention.

The cyclization of the amide of formula IV is advantageously carried out under conditions such as described for the cyclization of 6-methyl-2-methylaminopyridine to 5-methylimidazo[1,5-a]pyridine in J. Org. Chemistry 40, 1210(1975). Said cyclization may be achieved advantageously with a Lewis acid, such as polyphosphoric acid, phosphorous oxychloride, polyphosphate ester, optionally in an inert solvent such as toluene, at a temperature range of 25° to 150°, preferably 50° to 120° C.

The amides of formula IV are prepared by acylating a compound of formula V

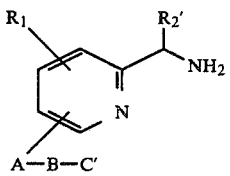

wherein $R_1$, $R_2'$, A, B and C' have meaning given above, with a carboxylic acid of the formula VI

 (VI)

wherein $R_2''$ has meaning given above, or with a reactive functional derivative thereof.

Reactive functional derivatives of compounds VI are preferably acid halides, simple or mixed anhydrides, such as the acid chloride, the acid anhydride $(R_2''CO)_2O$, or a mixed anhydride derived from a lower alkoxycarbonyl halide, such as ethyl chloroformate, or from a hindered lower alkanoyl halide, e.g., from pivaloyl chloride, by methods well-known to the art.

Said condensation of compounds V and VI (the acylation of V) occurs either spontaneously by e.g. heating with formic acid, or in the presence of condensing agents, e.g. disubstituted carbodiimides, such as dicyclohexylcarbodiimide.

The acylation of compounds of formula V with a reactive functional derivative of VI, e.g. acetyl chloride or acetic anhydride, occurs advantageously in the presence of an organic or inorganic base, e.g., potassium carbonate, triethylamine.

The amines of formula V may be obtained, e.g. from the corresponding substituted 2-(cyano, or lower hydroxyiminoalkyl) pyridines by reduction, e.g. by hydrogenation in the presence of a catalyst such as palladium on charcoal or by treatment with a chemical reducing agent such as borane or sodium cyanoborohydride, the reducing agent being chosen according to the type of other functional groups present in the molecule. The compounds of formula V may also be obtained by amination of the correspondingly substituted and reactively esterified 2-(hydroxymethyl)pyridines.

The compounds of the invention wherein A represents ethenylene or ethenylene substituted by lower alkyl can be prepared by (a) condensing a compound of formula VII

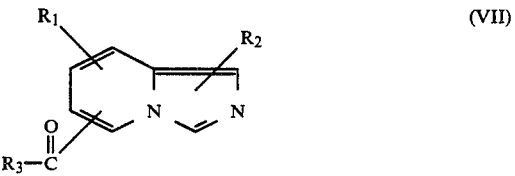

wherein $R_1$ and $R_2$ are as previously described and $R_3$ represents hydrogen or lower alkyl; with a compound of the formula VIII

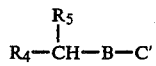 (VIII)

wherein $R_4$ represents hydrogen or lower alkyl; $R_5$ represents di-lower alkyl-phosphono, e.g. diethylphosphono, or triarylphosphoranyl, e.g. triphenylphosphoranyl; C' represents carboxy, lower alkoxycarbonyl, carbamoyl, mono- or di-(lower alkyl) substituted carbamoyl, cyano, halomethyl lower alkanoyloxymethyl, etherified hydroxymethyl, 5-tetrazolyl, 4,5-dihydro-2-oxazolyl, 4,5-dihydro-2-oxazolyl substituted by lower alkyl, or hydroxycarbamoyl; and B is as previously defined for said compounds of formula I; converting any resulting compound wherein C' differs from C into a compound of formula I; and, if desired converting any resulting compound of formula I into another compound of the invention.

The condensation as described is carried out under conditions used in the art for a Wittig type condensation, e.g. as described in J. Am. Chem. Soc. 83, 1733 (1961) under ylid forming conditions, e.g. in the presence of a strong base such as sodium hydride, in a solvent such as methylene chloride, toluene at a temperature ranging from −20° to +100°, preferably from −10° to +50°.

Certain compounds of formula I, e.g. wherein A represents a direct bond; B represents lower alkylenephenylene lower alkylene, lower alkylenephenylene, lower alkylene-(thio or oxy)-lower alkylene, lower alkylene-(thio or oxy)-phenylene, lower alkylenephenylene-lower alkenylene, or lower alkadienylene; may be prepared by condensing a compound of the formula IX

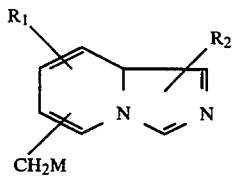

wherein M is an alkali metal; $R_1$ and $R_2$ represent hydrogen or lower alkyl, with a reactive functional derivative of a compound of the formula X

wherein B' represents lower alkylenephenylene-lower alkylene, lower alkylenephenylene, lower alkylene-(thio or oxy)-lower alkylene, lower alkylene-(thio or oxy)-phenylene, lower alkylenephenylene lower alkenylene, or lower alkadienylene; C' represents carboxy, trialkoxymethyl, unsubstituted or mono- or di-(lower alkyl) substituted carbamoyl, cyano, lower alkanoyloxymethyl, etherified hydroxymethyl, halomethyl, 4,5-dihydro-2-oxazolyl or 4,5-dihydro-2-oxazolyl substituted by lower alkyl, 5-tetrazolyl or hydroxycarbamoyl; to yield a compound of formula Ib

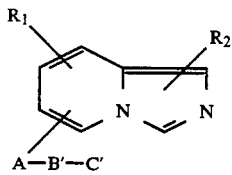

wherein A, B', C', $R_1$ and $R_2$ having meaning given above; converting any resulting product wherein C' differs from C, into a compound of formula I; and, if desired converting any resulting compound of formula I into another compound of this invention.

Reactive organometallic compounds of formula IX wherein M is an alkali metal are obtained by metallation of the appropriate methyl substituted imidazo[1,5-a]pyridine, e.g. 5-methylimidazo[1,5-a]pyridine, prepared as described in the Journal of Organic Chemistry 40, 1210 (1975), with a reactive metallating agent, e.g. butyl lithium or lithium diisopropylamide in an inert solvent such as tetrahydrofuran at a temperature below room temperature preferably at about −50°.

Condensation of the intermediate of formula IX with reactive functional derivatives of a compound of formula X proceeds at a temperature range preferably from about −75° to +50°. In the case where C' represents carboxy, 5-tetrazolyl, hydroxycarbamoyl mono(-lower-alkyl)carbamoyl, the appropriate metal salt, e.g. the lithium salt, of the reactive functional derivative of the corresponding compound of formula X is first prepared for the condensation with intermediate IX.

Certain terms used in the foregoing processes have the meanings as defined below.

Reactive functional derivatives of alcohols e.g. of formula X are e.g. such esterified by a strong inorganic or organic sulfonic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)methyl, particularly triethoxy- or trimethoxymethyl.

Etherified hydroxymethyl represents preferably tertiary lower alkoxymethyl, lower alkoxyalkoxymethyl such as methoxymethoxymethyl, 2-oxa- or 2-thiacycloalkoxymethyl particularly 2-tetrahydropyranyloxymethyl.

Lower alkylenedioxy represents preferably ethylenedioxy.

Halomethyl represents especially chloromethyl but may also be bromomethyl or iodomethyl.

Lower alkanoyloxymethyl represents preferably acetoxymethyl.

An alkali metal represents preferably lithium but may also be potassium or sodium.

The conversion of any initial product of the aforesaid processes wherein C' differs from C into a compound of formula I, and the optional conversion of any resulting product of formula I into another compound of this invention are performed by chemical methodology known to the art.

Hydrolysis of intermdiates wherein C' represents trialkoxymethyl to compounds of formula I wherein C is carboxy is advantageously carried out with inorganic acids such as hydrohalic or sulfuric acid. Hydrolysis of intermediates wherein C' represents etherified hydroxymethyl to compounds of formula I wherein B represents hydroxymethyl is preferably carried out with solutions of inorganic acids such a hydrohalic acid.

Intermediates of formula Ia or Ib wherein C' is halomethyl may be reacted preferably with a metal cyanide such as potassium cyanide in a conventional manner to yield the compounds of formula I wherein the chain is extended by 1 carbon atom and C is cyano. These in turn are converted to compounds of formula I wherein C is carboxy, alkoxycarbonyl or carbamoyl using methods known to the art.

Thus, the compounds of formula I wherein C represents cyano (nitriles) are converted to compounds of formula I wherein C is carboxy by hydrolysis with inorganic acids e.g. a hydrohalic acid such as hydrochloric acid or sulfuric acid in aqueous solution, or advantageously by hydrolysis with aqueous alkali metal hydroxide e.g. potassium hydroxide at reflux temperature.

The conversion of said nitriles to compounds of formula I wherein C represents lower alkoxycarbonyl is advantageously carried out by treatment first with a lower alkanol, e.g. anhydrous ethanol, in the presence of a strong acid, e.g. hydrochloric acid preferably at reflux temperature, followed by careful hydrolysis with water.

Furthermore the conversion of the said nitriles to compounds of formula I wherein C represents carbamoyl is preferably carried out by treatment with an alkali metal hydroxide, e.g. dilute sodium hydroxide, and hydrogen peroxide, preferably at room temperature.

Said nitriles of formula I may also be converted to compounds of formula I wherein C represents 5-tetrazolyl by condensation with a compound which serves as a source of hydrazoic acid, e.g. sodium azide or ammonium azide preferably in a polar solvent such as dimethylformamide and at a temperature range of about 75° to 150°.

Furthermore, the intermediates of formula Ia or Ib wherein C' is halomethyl, such as chloromethyl, are converted to compounds of formula I, wherein C is carboxy and the chain length is extended by two carbons, by first treating with e.g. a di-(lower)alkyl malonate, such as diethyl malonate, in the presence of a base such as potassium carbonate or sodium ethoxide, in a solvent such as dimethylformamide, preferably at a temperature range from 50° to 100°. The resulting substituted di(lower)alkyl malonate is hydrolyzed, advantageously with aqueous base, such as dilute sodium hydroxide, to the corresponding malonic acid which is decarboxylated under standard conditions, e.g. by heating in xylene solution, to give a compound of formula I wherein C is carboxy. Substitution of the di-(lower)alkyl malonate with a lower alkyl cyanoacetate yields the corresponding compounds of formula I wherein C is cyano.

Compounds of the invention, wherein B represents straight chain or branched alkenylene with a terminal double bond, may also be prepared from intermediates of formula Ia or Ib wherein C' is halomethyl. For instance, said intermediates are first treated with e.g. a lower alkyl ester of an α-(aryl- or alkyl)-thioacetic acid such as ethyl α-(phenylthio)-acetate, in the presence of a strong base such as sodium hydride. Subsequent oxidation of the resulting α-arylthio or α-alkylthio substituted ester to the α-arylsulfinyl or α-alkylsulfinyl ester with e.g. sodium periodate, followed by heat-induced elimination, by e.g. refluxing in xylene, yields a compound of general formula I (an α,β-unsaturated ester) wherein β represents e.g. alkenylene and C represents e.g. lower alkoxycarbonyl, and the chain length has been extended by two carbon atoms. Similarly, the compounds of formula Ia wherein C represents halomethyl may first be converted to the corresponding carboxaldehydes with e.g. dimethylsulfoxide in the presence of triethylamine and silver tetrafluoroborate. Subsequent Wittig condensation e.g. with ethyl (triphenylphosphoranylidene)-acetate also yields the above-cited α,β-unsaturated esters. Similar condensation with e.g. triethyl 4-phosphonocrotonate yields the corresponding compounds of formula I wherein B represents lower alka-dienylene and C represents lower alkoxycarbonyl.

Compounds of formula I wherein C is lower alkoxycarbonyl may be amidized with ammonia, mono- or di-(lower) alkylamines (e.g. methylamine, dimethylamine), hydroxylamine or 2-hydroxyethylamine optionally substituted by lower alkyl in an inert solvent, e.g. a lower alkanol, such as butanol, optionally at elevated temperatures to yield compounds of formula I wherein C represents unsubstituted, mono- or di-(lower) alkylcarbamoyl, hydroxycarbamoyl or dihydro-2-oxazolyl optionally substituted by lower alkyl.

The compounds of formula I wherein C represents unsubstituted carbamoyl may be dehydrated to the corresponding nitrile by treatment with e.g. phosphorus oxychloride or thionyl chloride in an inert solvent such as toluene.

Conversion of compounds of formula I wherein C is lower alkoxycarbonyl; cyano; unsubstituted, mono- or di-(lower alkyl)carbamoyl dihydro-2-oxazolyl optionally substituted by lower alkyl to compounds of formula I wherein C represents carboxy is advantageously carried out by hydrolysis with inorganic acids such as hydrohalic or sulfuric acid or with aqueous alkalis, preferably alkali metal hydroxides such as lithium or sodium hydroxide.

Compounds of formula I wherein C represents carboxy or lower alkoxycarbonyl may be reduced with simple or complex light metal hydrides such as lithium aluminum hydride, alane or diborane to compounds of formula I wherein C is hydroxymethyl. Said alcohols are also obtained by appropriate solvolysis of compounds of formula Ia or Ib wherein C' is halomethyl by treatment with e.g. an alkali metal hydroxide such as lithium or sodium hydroxide.

Said alcohols may in turn be transformed to the compounds of formula I wherein B is carboxy with conventional oxidizing agents, advantageously with pyridinium dichromate in dimethylformamide at room temperature.

Free carboxylic acids may be esterified with lower alkanols such as ethanol in the presence of a strong acid e.g. sulfuric acid advantageously at elevated temperature or with diazo (lower) alkanes, e.g. diazomethane in a solvent such as ethyl ether, advantageously at room temperature, to give the corresponding esters, namely compounds of formula I wherein C is lower alkoxycarbonyl.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di(lower) alkylamines, hydroxylamine, 2-hydroxyethylamine optionally substituted by lower alkyl in an inert solvent such as methylene chloride, preferably in the presence of a basic reagent such as pyridine, to compounds of formula I wherein C represents unsubstituted, mono or di-(lower)alkylcarbamoyl, hydroxycarbamoyl, or dihydro-2-oxazolyl optionally substituted by lower alkyl.

Compounds of formula I wherein C represents mono(lower) alkylcarbamoyl are converted to compounds of formula I wherein C is di-(lower)alkyl-carbamoyl by treatment of the former with a strong base e.g. sodium hydride followed by an alkylating agent, e.g. a lower alkyl halide in an inert solvent, e.g. dimethylformamide.

The intermediate of formula Ia wherein C' represents halo attached to phenyl in group B, may be converted to compounds of formula I wherein B contains a phenylene-lower alkenylene moiety and C represents lower alkoxycarbonyl by treatment with an α,β-unsaturated ester such as methyl methacrylate in the presence of a palladium salt, e.g. palladium acetate and a tri-arylphosphine, such as tri-o-tolylphosphine.

The compounds of formula I, wherein B represents lower alkylene-(thio or oxy)-phenylene, phenylene-(thio or oxy)-lower alkylene or lower alkylene-(thio or oxy)-lower alkylene, may also be prepared by condensation of intermediates corresponding to formula Ia wherein B represents lower alkylene or phenylene and C' represents hydroxymethyl (as reactive functional derivatives thereof such as halomethyl) with a lower alkanol or (thiol), or with a phenol (or thiophenol) appropriately substituted by C (or a temporarily protected C') preferably in the presence of a strong base such as sodium hydroxide.

Compounds of formula I or appropriate intermediates are converted to the corresponding 5, 6, 7, 8-tetrahydroimidazo[1,5-a]pyridine compounds by reduction with hydrogen in the presence of a hydrogenation catalyst, e.g palladium, and an acid e.g. a mineral acid, for instance hydrochloric acid in an inert solvent, e.g. ethanol.

Furthermore compounds of formula I wherein B represents e.g., phenylene-lower alkenylene may be converted by catalytic hydrogenation, advantageously under neutral conditions e.g. with palladium catalyst at atmospheric pressure in an inert solvent, e.g. ethanol, to compounds of formula I wherein B represents e.g. phenylene-lower alkylene.

Furthermore compounds of formula I wherein $R_1$ and $R_2$ represent hydrogen can be converted to the corresponding halo derivatives by direct halogenation with chlorine, bromine or iodine.

Compounds of formula I and intermediates wherein $R_1$ is aryl-lower alkoxy, e.g. benzyloxy, or lower alkoxy, e.g. methoxy, can be converted to compounds wherein $R_1$ is hydroxy by hydrogenolysis or hydrolysis respectively, using methods well known in the art.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure, and with temporary protection of reactive functional groups as required.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of isomers, such as racemates, mixtures of diastereoisomers, mixtures of racemates or mixtures of geometrical isomers.

Resulting mixtures of diastereoisomers, mixtures of racemates and geometric isomers can be separated on the basis of the physicochemical differences of the constituents, in known manner, into the pure isomers, diastereoisomers, racemates, or geometric isomers for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates.

Advantageously, the more active of the two antipodes is isolated.

Finally, the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein C represents carboxy, 5-tetrazolyl or hydroxycarbamoyl can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a coresponding salt is also intended, provided such is possible or appropriate under the circumstances.

The compounds, including their salts, can also be obtained in the form of their hydrates, or include other solvents used for the crystallisation.

The pharmaceutical compositions according to the invention are those suitable for enteral, such as oral or rectal, and parenteral administration to mammals, including man, for the treatment or prevention of diseases responsive to inhibition of thromboxane synthetase such as peripheral vascular diseases, comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 200 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To a stirred suspension of 150 mg of sodium hydride in 25 ml of toluene is added 550 mg of triethyl 4-phosphonocrotonate in a dropwise manner over a 10-minute period. The reaction mixture is maintained at 5° by cooling in an ice-water bath. On completion of the addition, 300 mg of 5-formylimidazol[1,5-a]pyridine is added to the reaction mixture which is then allowed to stir at room temperature for 1 hour. The reaction mixture is poured into 100 ml of ice water and extracted with 2×100 ml of ethyl acetate. The ethyl acetate extracts are combined and dried over magnesium sulfate, filtered and evaporated to dryness to yield an oily residue. This is purified by column chromatography on silica gel using a mixture of diethyl ether and ethyl acetate as eluent. Evaporation of the solvent under reduced pressure yields 5-(4-ethoxycarbonylbuta-1,3-dienyl)-imidazo[1,5-a]pyridine melting at 101°–103°.

The starting material is prepared as follows. p To a solution of 18 g of 3-ethylthioimidazo[1,5-a]pyridine [Blatcher and Middlemiss, Tet.Lett. (21) 2195 (1980)] in 200 ml of tetrahydrofuran at −50° is added a solution of 80 ml of 1.6M n-butyl lithium in hexane in a dropwise manner over a period of 30 minutes. On completion of the addition, the reaction mixture is allowed to stir at −50° for a further 45 minutes and 10 ml of dimethylformamide is added dropwise to the cooled solution over a period of 10 minutes. On completion of the addition, the reaction mixture is allowed to warm to room temperature and is poured into 500 ml of ice water.

The mixture is extracted with 500 ml of diethyl ether and the ethereal extract is dried over anhydrous magnesium sulfate, filtered and the solvent evaporated under reduced pressure to yield an oily residue. This is purified by column chromatography on silica gel using a mixture of diethyl ether and hexane (1:2) as eluent. Evaporation of the solvent yields 5-formyl-3-ethylthioimidazo[1,5-]pyridine melting at 41°–42°.

To a solution of 20 g of 5-formyl-3-ethylthioimidazo[1,5-a]pyridine in 200 ml of isopropanol is added approximately 15 g of Raney nickel. The reaction mixture is stirred and heated at reflux temperature for 16 hours. The catalyst is removed by filtration through celite. The filtrate is evaporated under reduced pressure to yield an oily residue. This is purified by column chromatography on silica gel using a mixture of diethyl ether and ethyl acetate (2:1) as eluent. Evaporation of the solvent under reduced pressure yields 5-formylimidazo[1,5-a]pyridine melting at 138°–140°.

EXAMPLE 2

To a solution of 200 mg of 5-(4-ethoxycarbonylbuta-1,3-dienyl)imidazo[1,5-a]pyridine in 20 ml of methanol is added 4 ml of 1N sodium hydroxide. The reaction mixture is stirred at room temperature for 18 hours. The methanol is evaporated under reduced pressure and the residue diluted with 20 ml of water and the solution is adjusted to pH 5 with hydrochloric acid. The precipitate is collected to give 5-(4-carboxybuta-1,3-dienyl)-imidazo[1,5-a]pyridine, melting at 243°–245°.

EXAMPLE 3

A solution of 0.34 g of 5-(p-bromophenyl)imidazo[1,5-a]pyridine, 2.7 mg of palladium acetate, 7.5 mg of tri-o-tolyphosphine and 0.22 g methyl methacrylate in 3 ml of triethylamine is refluxed for 7 days, diluted with 50 ml of methylene chloride and washed with water. The methylene chloride is evaporated and the residue is taken up in 50 ml ether, filtered and washed with 2×20 ml of ice-cold 0.5N hydrochloric acid. The aqueous phase is adjusted to pH=8 and is extracted with methylene chloride. The methylene chloride extract is dried over magnesium sulfate and evaporated. Preparative thin layer chromatography (silica gel, ether) yields 5-[p-(2-carbomethoxyprop-2-enyl)phenyl]imidazo[1,5-a]pyridine; Rf=0.37; NMR: (CDCl$_3$) 5.62 (s, 1H), 6.32 (s, 1H); IR (CH$_2$Cl$_2$) 1720 cm$^{-1}$.

The starting material is prepared as follows:
To a solution of 2.54 g of 2-(p-bromophenyl)pyridine (prepared as described in J. Chem. Soc. (1940) 349, 355) in 25 ml of acetic acid is added slowly 1.6 ml of 40% peracetic acid. The mixture is heated at 80°–85° for 2 hours and excess peracid is destroyed at 25° with saturated sodium sulfite solution. The acetic acid is evaporated. The residue is taken up in 30 ml of methylene chloride, filtered and the solvent evaporated. The resulting 2-(p-bromophenyl)pyridine-N-oxide is treated with 1.47 g of dimethyl sulfate in 15 ml of toluene at 80°–90° for 2 hours. Evaporation of solvent yields the methyl sulfate salt which is dissolved in 3.5 ml of ice-cold water. A solution of 2.17 g of potassium cyanide and 1.6 ml of 1N sodium hydroxide in 3.5 ml of ice-cold water is added at such a rate as to keep the temperature at 0°. After 16.5 hours at 0°, the product is extracted with 3×50 ml aliquots of methylene chloride; the extract is dried over sodium sulfate and the solvent is evaporated to an oil which is chromatographed on 45 g of silica gel with ether as the eluent to yield of 2-(p-bromophenyl)-6-cyanopyridine melting at 76°–78°.

To a refluxing solution of 1.6 g of 2-(p-bromophenyl)-6-cyano pyridine in 8 ml of tetrahydrofuran is added slowly a solution of 0.92 ml of borane-dimethylsulfide in 6 ml. of tetrahydrofuran. Dimethyl sulfide is simultaneously removed by distillation through a 10 cm vigreux column. The mixture is refluxed for 15 minutes after the addition is complete, cooled to 30°, and 6 ml of 6N hydrochloric acid is added. After hydrogen evolution has ceased, the reaction is refluxed for 30 minutes, cooled to 0°, saturated with solid sodium carbonate and extracted with 4×50 ml aliquots of methylene chloride. The methylene chloride solution is evaporated and the residue is chromatographed through 10.0 g of silica gel with 1:1 methanol-ethyl acetate as eluent to yield 2-aminomethyl-6-(p-bromophenyl)pyridine melting at 71°–75°.

A solution of 0.4 g of 2-aminomethyl-6-(p-bromophenyl)pyridine in 1.0 ml of formic acid is heated at 90° for 18 hours, cooled to 0°, made basic with saturated ammonium hydroxide solution and extracted with methylene chloride (4×10 ml). The extracts are dried and evaporated to yield crude 2-formylaminomethyl-6-(p-bromophenyl)pyridine, m.p. 115°–119°, which is redissolved in 1.4 ml of toluene and heated at 90° with 0.65 g of phosphorus oxychloride for 18 hours. Evaporation of the excess phosphorus oxychloride and toluene, basification with saturated ammonium hydroxide and extraction with 4×15 ml aliquots of methylene chloride followed by evaporation of the solvent yields a crude product. Purification by chromatography on silica gel using ethyl acetate as the eluent and evaporation of the solvent yields 5-(p-bromophenyl)-imidazo[1,5-]pyridine, melting at 55°–57°.

EXAMPLE 4

A solution of 20 mg of 5-[p-(2-carbomethoxyprop-2-enyl)phenyl]imidazo[1,5-a]pyridine and 20 mg of sodium methoxide in 2 ml. of methanol is stirred under nitrogen for 1 hour at 25°. To the reaction mixture 2 ml. of water is added, and the homogenous solution is stirred at room temperature for 18 hours. The solvent is evaporated and the residue is redissolved in 5 ml of water and washed with 3 ml of ether. Acidification to pH=5, extraction with 10 ml of methylene chloride, drying over magnesium sulfate and evaporation yields 5-[p-(2-carboxyprop-2-enyl)phenyl]imidazo[1,5-a]pyridine, m.p. 171°–172°.

EXAMPLE 5

To a solution of lithium diisopropylamide (prepared from 3.8 ml of n-butyllithium in hexane and 0.84 ml of diisopropylamine) in 10 ml tetrahydrofuran at −70° C., is added 1.35 g of triethyl 4-phosphonocrotonate in a dropwise manner over a 15 minute period. On completion of the addition, 6.0 g of 5-(5-formylpentyl)imidazo[1,5-a]pyridine is added in a dropwise manner. The reaction mixture is allowed to stir at room temperature for 15 minutes. The reaction mixture is quenched with methanol and the solvent evaporated under reduced pressure to yield 5-(9-ethoxycarbonyl-nona-6,8-dienyl)-imidazo[1,5-a]pyridine as an oil.

The starting material is obtained as follows:

To a solution of 50 g of 5-methylimidazo[1,5-a]pyridine [J. Org. Chem. 40, 1210 (1975)] in 625 ml of tetrahydrofuran precooled to −75° is added, under nitrogen atmosphere, 175 ml of 2.4N n-butyllithium in hexane while maintaining temperature below −53°. The solution of 5-(lithiomethyl)imidazo[1,5-a]pyridine, is cooled back to −75° and a solution of 121.8 g of 5-bromo-1,1,1-triethoxypentane in 125 ml of tetrahydrofuran is added rapidly at which time the temperature rises to −60°. The reaction mixture is allowed to warm to −4° over a 45 minute period and evaporated practically to dryness. The residue is partitioned between 500 ml of ethyl ether and 240 ml of 3N hydrochloric acid. The ether solution is further extracted twice with 60 ml of 3N hydrochloric acid; the combined aqueous extract is basified with 100 ml of concentrated ammonia hydroxide and reextracted twice with 200 ml of ethyl ether. The ether extract is dried over magnesium sulfate and evaporated to dryness to give an oil which is distilled under high vacuum to give 5-(5-ethoxycarbonylpentyl)-imidazo[1,5-a]pyridine boiling at 180°–5°/0.12 mm Hg.

A suspension of 26 g of 5-(5-ethoxycarbonylpentyl)imidazo[1,5-a]pyridine in 100 ml of 1N aqueous sodium hydroxide solution is heated on a steam bath for two hours; 10 ml of ethanol is added and heating is continued for 45 minutes. The reaction mixture is cooled, washed with 300 ml of ether and the solution is adjusted to pH 5.5 with concentrated hydrochloric acid. The crystallized product is collected to yield 5-(5-carboxypentyl)-imidazo[1,5-a]pyridine melting at 144°–147°.

To a cooled (−60°) solution of 4.9 g of 5-(5-methoxycarbonylpentyl)-imidazo[1,5-a]pyridine [obtained by esterification of 5-(5-carboxypentyl)-imidazo[1,5-a]pyridine with diazomethane in methylene chloride] in 140 ml of methylene chloride is added 40 ml of a 1.75M solution of diisobutyl aluminum hydride in hexane in a dropwise manner over a 20 minute period. On completion of the addition, the reaction is allowed to stir at −60° for a further 20 minutes. Then, 10 ml of methanol, followed by 100 ml of water, are added to quench the reaction. The reaction mixture is stirred at room temperature for 15 minutes, the methylene chloride layer is separated and the solvent evaporated under reduced pressure to yield 5-(5-formylpentyl)imidazo[1,5-a]pyridine as an oil; NMR (CDCl$_3$) 9.7 (m, 1H); IR (CH$_2$Cl$_2$) 1710 cm$^{-1}$.

EXAMPLE 6

To a solution of 6 g 5-(9-ethoxycarbonylnona-6,8-dienyl)imidazo[1,5-a]pyridine in 30 ml of methanol is added 6 ml of 1N sodium hydroxide. The reaction is allowed to stir at room temperature for 3 hours. The methanol is evaporated under reduced pressure and the residue diluted with 15 ml water and the solution adjusted to pH 7 with 1N hydrochloric acid. The solution is extracted with 2×150 ml of ethyl acetate. The combined ethyl acetate extracts are dried over magnesium sulfate, filtered and the solvent evaporated under reduced pressure to yield 5-(9-carboxynona-6,8-dienyl)imidazo[1,5-a]pyridine melting at 120°–122°.

EXAMPLE 7

A solution of 2-(p-ethoxycarbonylphenyl)-6-formylaminomethylpyridine (9.89 g) and phosphorus oxychloride (11.15 g) in 26 ml of toluene is heated at 90° for 15 hours. The solvent is evaporated and the residue taken up in 50 ml of methylene chloride, cooled to 0° and made basic with excess ice-cold saturated ammonium hydroxide solution. The organic phase is separated, dried and evaporated. The residual solid is passed through 100 g of silica gel with ethyl acetate as eluent to yield after crystallization from ethyl acetate 5-(p-(ethoxycarbonylphenyl)-imidazo[1,5-a]pyridine, m.p. 118°–119°.

The starting material is prepared as follows:

Peracetic acid (40%, 8.9 ml) is added dropwise to 2-(p-ethoxycarbonylphenyl)-pyridine (14.08 g) so as to maintain the reaction between 80° and 85°. After the addition is complete the reaction is heated at 90° for 3 hours, allowed to cool to room temperature and excess peracetic acid is destroyed with aqueous sodium sulfite. The solvent is evaporated and the residue taken up in methylene chloride and refiltered through celite. Evaporation yields 2-(p-ethoxycarbonylphenyl)pyridine-N-oxide which is treated with dimethyl sulfate (8.66 g) in 62 ml of toluene at 90° for 3 hours. The solvent is evaporated and the residue redissolved in an ice-cold mixture of 8 ml of water and 9.3 ml of 1N sodium hydroxide. A solution of potassium cyanide (13.64 g) in 10 ml of water is added slowly and the reaction mixture is maintained at 0° for 24 hours. Extraction with methylene chloride (2×30 ml), drying over sodium sulfate and evaporation of solvent yields 6-cyano-2-(p-ethoxycarbonylphenyl)-pyridine; IR (CH$_2$Cl$_2$) 2200 cm$^{-1}$.

2-(p-Ethoxycarbonylphenyl)-6-cyanopyridine (16.23 g) is hydrogenated at atmospheric pressure in 254 ml of methanol with 12.9 ml of concentrated hydrochloride acid and 2.63 g of 10% palladium on charcoal until 2 molar equivalents of hydrogen have been consumed. Sodium methoxide (6.9 g) is added and the catalyst is filtered off. The solvent is evaporated. The residue is redissolved in 20 ml of methylene chloride and the salts are removed by filtration. Evaporation of the solvent yields a solid which is recrystallized from chloroform to yield 6-aminomethyl-2-(p-ethoxycarbonylphenyl)pyridine, m.p. 141°–143°.

A solution of 6-aminomethyl-2-(p-ethoxycarbonylphenyl)pyridine (10.76 g) in 10 ml of formic acid is heated at 90° for 15 hours. The reaction is cooled to 0°, basified with excess saturated ammonium hydroxide solution and extracted with chloroform (4×30 ml). The organic extracts are dried and evaporated to yield 2-(p-ethoxycarbonylphenyl)-6-formylaminomethylpyridine which is recrystallized from toluene, m.p. 119.5°–120.5°.

EXAMPLE 8

A solution of 5-(p-ethoxycarbonylphenyl)-imidazo[1,5-a]pyridine (1.0 g) in 10 ml of ethanol and 10 ml of 1N sodium hydroxide is refluxed for 3 hours. The ethanol is evaporated. The aqueous phase is washed with ether, adjusted to pH=6 and the solid collected to yield 5-(p-carboxyphenyl)imidazo[1,5-a]pyridine.

EXAMPLE 9

5-(p-Ethoxycarbonylphenyl)-imidazo[1,5-a]pyridine (1.0 g) is dissolved in 26 ml of methylene chloride at −78° under nitrogen and 6.6 ml of diisobutylaluminum hydride in toluene (11.4 mmole) is added dropwise. After stirring for 1 hour, 1.5 ml of methanol is added, the cold bath is removed and 15 ml of water is added. The salts are filtered off, the organic phase is dried over sodium sulfate and evaporated to yield 5-(p-hydroxymethylphenyl)imidazo[1,5-a]pyridine, m.p. 137°–138°.

EXAMPLE 10

A solution of 5-(p-hydroxymethylphenyl)imidazo[1,5-a]pyridine (0.52 g) in 10 ml of methylene chloride is refluxed with 5.2 g of activated manganese dioxide for 24 hours. An additional 5.2 g of manganese dioxide is added and the reaction mixture is refluxed an additional 6 hours, filtered, and the solvent is evaporated to yield 5-(p-formylphenyl)-imidazo[1,5-a]pyridine, m.p. 144°–146°.

EXAMPLE 11

(a) Triethyl 2-phosphonopropionate (0.61 g) is added to a solution of lithium diisopropylamide (from 0.32 g of diisopropylamine and 1.7 ml of 1.64M n-butyllithium) in 20 ml of tetrahydrofuran at 0° under nitrogen. After stirring for 10 minutes, 5-(p-formylphenyl)-imidazo[1,5-a]pyridine (0.50 g) is added dropwise in a solution of 5 ml of tetrahydrofuran. The reaction mixture is stirred for two hours at 0° and quenched with 25 ml of water. The layers are separated and aqueous phase is extracted with ethyl acetate (2×10 ml). The organic phases are combined, dried over sodium sulfate, filtered and evaporated to yield an oil which is chromatographed on silica gel with ethyl acetate as eluent to yield 5-[p-(2-ethoxycarbonylprop-1-enyl)phenyl]imidazo[1,5-a]pyridine; IR (CH$_2$Cl$_2$) 1700 cm$^{-1}$.

(b) 5-[p-(2-ethoxycarbonyleth-1-enyl)phenyl]imidazo[1,5-a]pyridine can be similarly prepared by condensation of triethyl 2-phosphonoacetate with 5-(p-formylphenyl)imidazo[1,5-a]pyridine.

EXAMPLE 12

(a) A solution of 5-[p-(2-ethoxycarbonylprop-1-enyl)-phenyl]imidazo[1,5-a]pyridine (0.60 g) in 2 ml of ethanol and 6.2 ml of 1N sodium hydroxide is refluxed for 3 hours, cooled and evaporated. The residue is partitioned between 5 ml of water and 1 ml of ethyl acetate. The aqueous phase is acidified (pH=2) with concentrated hydrochloric acid and the resulting solid is filtered off to yield 5-[p-(2-carboxyprop-1-enyl)phenyl]imidazo[1,5-a]pyridine hydrochloride, m.p. 280°–282°.

(b) 5-[p-(2-carboxyeth-1-enyl)phenyl]imidazo[1,5-a]pyridine can be similarly prepared by hydrolysis of 5-[p-(2-ethoxycarbonyleth-1-enyl)phenyl]imidazo[1,5-a]pyridine.

EXAMPLE 13

5-(p-carboxyphenethyl)-imidazo[1,5-a]pyridine (2.66 g) is dissolved in 100 ml of dry tetrahydrofuran at 0° and 20 ml of 1M borane tetrahydrofuran complex in tetrahydrofuran (20 ml) is added dropwise. The reaction mixture is stirred at room temperature for two hours, and 20 ml of acetic acid and 20 ml of methanol are added carefully. The mixture is refluxed for 1 hour, cooled and evaporated, the resulting oil is partitioned between ether and 1N sulfuric acid. The aqueous phase is separated, adjusted to pH=8 and extracted with ethyl acetate the extract is dried over sodium sulfate and evaporated to yield 5-[p-(hydroxymethyl)phenethyl]imidazo[1,5-a]pyridine.

EXAMPLE 14

Potassium cyanide (11.18 g) and dibenzo-18-crown-6(1.0 g) are added to a solution of 5-[p-(chloromethyl)-phenethyl]imidazo[1,5-a]pyridine (9.5 g) in 300 ml of dry acetonitrile under nitrogen. The mixture is refluxed for 24 hours, the solvent is evaporated and the residue partitioned between methylene chloride and water. The organic phase is separated, dried and evaporated to yield 5-[p-(cyanomethyl)phenethyl]imidazo[1,5-a]pyridine.

The starting material is prepared as follows:

5-[p-(hydroxymethyl)phenethyl]imidazo[1,5-a]pyridine (2.52 g) is refluxed in 20 ml of thionyl chloride for 2 hours. Excess thionyl chloride is evaporated and the residue is partitioned between ethyl acetate and dilute sodium bicarbonate solution. The organic phase is dried over sodium sulfate and evaporated to yield 5-[p-(chloromethyl)-phenethyl]imidazo[1,5-a]pyridine.

EXAMPLE 15

A solution of 5-[p-(cyanomethyl)phenethyl]imidazo[1,5-a]pyridine (1.0 g) in 2N sodium hydroxide (30 ml) is heated under reflux for 15 hours, acidified with concentrated sulfuric acid and filtered to yield 5-[p-carboxymethyl)phenethyl]imidazo[1,5-a]pyridine.

EXAMPLE 16

5-[p-(Hydroxymethyl)phenethyl]imidazo[1,5-a]pyridine (2.52 g) is refluxed in 100 ml of methylene chloride with 25.2 g of activated manganese dioxide for 24 hours. The mixture is filtered and evaporated to yield 5-(p-formylphenethyl)imidazo[1,5-a]pyridine.

EXAMPLE 17

Triethyl 2-phosphonopropionate (0.61 g) is added to a solution of lithium diisopropylamide (from 0.32 g of diisopropylamine and 1.7 ml of 1.64M n-butyllithium) in 20 ml of dry tetrahydrofuran at 0° under nitrogen. After stirring at 0° for 15 minutes 5-(p-formylphenethyl)-imidazo[1,5-a]pyridine (0.55 g) is added in 5 ml of tetrahydrofuran and the reaction mixture is stirred for 1 hour at 0° and 1 hour at 25° before quenching with 25 ml of water. The layers are separated and the organic phase is dried and evaporated. The resulting oil is redissolved in ethyl acetate and passed through a column of silica gel to remove the excess phosphonate and to yield 5-[p-(2-ethoxycarbonylprop-1-enyl)phenethyl]imidazo[1,5-a]pyridine.

EXAMPLE 18

5-[p-(2-Ethoxycarbonylprop-1-enyl)phenethyl]imidazo[1,5-a]pyridine (0.33 g) in 10 ml of 0.5N sodium hydroxide is refluxed for 3 hours, cooled and extracted with ether. The aqueous phase is adjusted to pH=6 and the resulting solid is filtered off to yield 5-[p-(2-carboxyprop-1-enyl)phenethyl]imidazo[1,5-a]pyridine.

EXAMPLE 19

Ethyl mercaptoacetate (2.19 g) is slowly added to a slurry of sodium hydride (0.87 g, 50% dispersion in mineral oil) in 30 ml of dry dimethylformamide at 5° under nitrogen. The ice bath is removed and, after stirring at room temperature for 30 minutes, 5-(5-chlorobutyl)imidazo[1,5-a]pyridine (3.47 g) is added in 15 ml of dimethylformamide. After 15 hours, the mixture is poured into 150 ml of water, made acidic (pH=2) and diluted with 100 ml of ether. The layers are separated and the aqueous phase is adjusted to pH=8 and extracted with methylene chloride. Drying of the extract and evaporation yields 5-[4-(ethoxycarbonylmethylthio)butyl]imidazo[1,5-a]pyridine; IR 1730, 1640 cm$^{-1}$.

EXAMPLE 20

5-[4-(Ethoxycarbonylmethylthio)butyl]imidazo[1,5-a]pyridine (4.4 g) in 30 ml of ethanol and 61 ml of 1.0N sodium hydroxide is heated under reflux for 3 hours. The ethanol is evaporated, the aqueous is extracted with ethyl acetate (20 ml) and the pH adjusted to 5. The resulting oil is crystallized from ethanol to yield 5-[4-(carboxymethylthio)butyl]imidazo[1,5-a]pyridine, m.p. 124°–126°.

EXAMPLE 21

A solution of 5-(4-chlorobutyl)imidazo[1,5-a]pyridine (5.20 g) is heated at 50° in 80 ml of dimethylformamide for 15 hours with the sodium salt of ethyl p-hydroxybenzoate [from ethyl p-hydroxybenzoate (4.55 g) and 50% sodium hydride (1.31 g)]. The reaction mixture is cooled, poured onto 100 g of ice, made acidic and extracted with ether (50 ml). The aqueous phase is brought to pH=8 and extracted with ether (3×100 ml). The organic extracts are combined, dried and evaporated to yield 5-[4-(p-ethoxycarbonylphenoxy)butyl]imidazo[1,5-a]pyridine, m.p. 85°–87° (crystallized from ether).

The starting material is prepared as follows:
A solution of 27 g of 1-bromo-3-chloropropane in 20 ml of dry tetrahydrofuran is added to a solution of 5-(lithiomethyl)-imidazo[1,5-a]pyridine (prepared from 22 g of 5-methylimidazo[1,5-a]pyridine and 90 ml of 2.3N solution of n-butyl lithium in hexane in tetrahydrofuran at below −50° while maintaining the temperature below −50°. The reaction mixture is stirred for 2 to 3 hours at −50°, allowed to warm to room temperature, stirred overnight, and evaporated to dryness.

The solution of the residue in methylene chloride is washed with water, dried over magnesium sulfate and evaporated to dryness to give the 5-(4-chlorobutyl)-imidazo[1,5-a]pyridine which is used without further purification.

EXAMPLE 22

A solution of crude 5-[4-(p-ethoxycarbonylphenoxy)-butyl]imidazo[1,5-a]pyridine (6.5 g) in 30 ml of ethanol and 30 ml of 1N sodium hydroxide is heated under reflux for 3 hours. After refluxing the ethanol is evaporated, the aqueous phase is extracted with ether, acidified to pH=2 and the resulting solid is filtered off to yield 5-[4-(p-carboxyphenoxy)butyl]imidazo[1,5-a]pyridine hydrochloride, m.p. 266°–268° dec.

EXAMPLE 23

5-[p-(2-Carboxyeth-1-enyl)phenyl]imidazo[1,5-a]pyridine (2.64 g) is dissolved in 50 ml of dry ethanol and hydrogenated at 3 atmospheres with 0.5 g of 5% palladium on charcoal until one molar equivalent of hydrogen is consumed. Filtration and evaporation yields 5-[p-(2-carboxyethylphenyl)imidazo[1,5-a]pyridine.

EXAMPLE 24

(a) A solution of 5-formylimidazo[1,5-a]pyridine (1.46 g) in 15 ml of dry dimethylsulfoxide is added to a solution of sodium 5-(triphenylphosphoranyl)valerate (4.4 g) in 50 ml of dry dimethylsulfoxide at room temperature (Helv. Chem. Acta 63 1430 (1980)). The reaction is stirred for 3 hours, hydrolyzed with water and neutralized with dilute sulfuric acid. Extraction with ethyl acetate and chromatography or silica gel yields 5-(5-carboxypent-1-enyl)-imidazo[1,5-a]pyridine.

(b) Similarly 5-[2-(p-caboxyphenyl)ethen-1-yl]-imidazo[1,5-a]pyridine can be prepared from sodium p-(triphenylphosphoranylmethyl)benzoate and 5-formylimidazo[1,5-a]pyridine.

EXAMPLE 25

5-[2-(p-Carboxyphenyl)ethen-1-yl]imidazo[1,5-a]pyridine (2.0 g) is hydrogenated in 50 ml of ethanol with 1.0 g of 5% palladium on charcoal at 3 atmospheres until a molar equivalent of hydrogen has been consumed. Filtration through celite and evaporation of solvent yields 5-[2-(p-carboxyphenethyl]imidazo[1,5-a]pyridine.

EXAMPLE 26

A solution of 5-[2-(p-hydroxyphenyl)ethen-1-yl]imidazo[1,5-a]pyridine (2.36 g) in 10 ml of dimethylformamide is added to a slurry of 0.5 g of sodium hydride in 30 ml of dry dimethylformamide at 0° under nitrogen. After warming to room temperature ethyl bromoacetate (1.67 g) is added and the reaction is heated to 60° for 5 hours. Water (200 ml) is added and the solution is extracted with ethyl acetate. The combined organic phases are washed with water, dried over sodium sulfate and evaporated to yield 5-[2-(p-[ethoxycarbonylmethoxy]phenyl)ethen-1-yl]imidazo[1,5-a]pyridine.

The starting material is prepared as follows:
Imidazo[1,5-a]pyridine-5-methyltriphenylphosphonium chloride (4.29 g), which is prepared from equimolar quantities of triphenylphosphine and 5-chloromethylimidazo[1,5-a]pyridine, is added to slurry of sodium hydride (0.5 g, 50% mineral oil dispersion) in 100 ml of dry tetrahydrofuran at 0° under nitrogen. After 1 hour at 0° a solution of p-hydroxybenzaldehyde (0.61 g) in 15 ml of dry tetrahydrofuran is added. The reaction is allowed to warm to room temperature, is then refluxed for 1 hour, cooled and acidified with dilute sulfuric acid. The aqueous layer is washed with ethyl acetate, adjusted to pH=7 with 50% sodium hydroxide and extracted with ethyl acetate. The organic phase is dried over sodium sulfate and evaporated to yield 5-[2-(p-hydroxyphenyl)-ethen-1-yl]-imidazo[1,5-a]pyridine.

5-Chloromethylimidazo[1,5-a]pyridine is prepared from 5-formylimidazo-[1,5-a]pyridine by reduction with sodium borohydride to 5-hydroxymethylimidazo[1,5-a]pyridine and subsequent treatment with thionyl chloride.

EXAMPLE 27

5-[2-(p-[Ethoxycarbonylmethoxy]phenyl)-ethen-1-yl]imidazo[1,5-a]pyridine (3.2 g) is refluxed in 30 ml of ethanol with 20 ml of 1N sodium hydroxide for 3 hours. The ethanol is evaporated and the aqueous phase is adjusted to pH=6. Filtration yields the substituted phenoxyacetic acid 5-[2-(p-carboxymethoxy]phenyl)ethen-1-yl]imidazo[1,5-a]pyridine.

EXAMPLE 28

A solution of 5-[p-(cyanomethyl)phenethyl]-imidazo[1,5-a]pyridine (6.0 g) in 16 ml of dry dimethylformamide is heated at 120° for 15 hours with sodium azide (2.15 g), lithium chloride (0.2 g) and ammonium chloride (1.80 g). After cooling and filtering, the solvent is evaporated and the residue is dissolved in 50 ml of water, extracted with 25 ml of ethyl acetate and brought to pH=5 with concentrated sulfuric acid. The precipitated solid is filtered, washed with water and dried to yield 5-[p-(5-tetrazolylmethyl)phenethyl]-imidazo[1,5-a]pyridine.

EXAMPLE 29

Preparation according to methods analogous to those described in the previous examples of compounds of formula I wherein A is a direct bond and $R_2$ is hydrogen.

| Compound | B | C | $R_1$ |
|---|---|---|---|
| a | 5-$(CH_2)_3OCH_2CH_2$ | COOH | H |
| b | 5-$(CH_2)_3SCH_2CH_2$ | COOH | 6-$OCH_2C_6H_5$ |
| c | 5-$(CH_2)_2$-p-$C_6H_4$—$CH_2$ | COOH | H |
| d | 5-$CH_2CH_2O$—p-$C_6H_4$ | COOH | H |
| e | 7-$CH_2CH_2O$—p-$C_6H_4$ | COOH | H |

The starting halo (bromo) compounds for condensation with the 5-methylimidazo[1,5-a]pyridine compounds to prepare compounds, a, b and d are described in U.S. Pat. No. 3,984,459, Chem. Abstracts 83, 166177b and U.S. Pat. No. 2,790,825 respectively.

The starting 6-benzyloxy-5-methylimidazo[1,5-a]pyridine for compound b is prepared as follows:

A solution of 3-benzyloxy-6-hydroxymethyl-2-methylpyridine (8.54 g) in 53 ml of thionyl chloride is refluxed for two hours and the thionyl chloride is removed by distillation. The residue is poured onto 50 g of ice, made basic with saturated sodium bicarbonate solution and extracted with ethyl acetate (3×50 ml). The organic extracts are dried over sodium sulfate and evaporated to give a yellow oil identified as 3-benzyloxy-6-chloromethyl-2-methylpyridine; NMR: ($CDCl_3$) 2.47 (3H), 4.54 (2H), 4.97 (2H).

A solution of 3-benzyloxy-6-chloromethyl-2-methylpyridine (8.02 g) and sodium azide (5.98 g) in 400 ml of ethanol is heated at 80° for 4 hours. The reaction mixture is cooled, filtered and evaporated to yield a residue which is partitioned between ice-cold 0.5N NaOH (150 ml) and ether (150 ml). The organic phase is dried over sodium sulfate and evaporated to yield 6-azidomethyl-3-benzyloxy-2-methylpyridine, NMR: δ($CDCl_3$) 2.47 (3H), 4.27 (2H), 4.95 (2H).

Lithium aluminum hyride (1.27 g) is added to a solution of 6-azidomethyl-3-benzyloxy-2-methylpyridine (7.18 g) in 120 ml of dry ether at room temperature. After stirring for 45 minutes, 1.3 ml of water, 1.3 ml of 15% sodium hydroxide and 3.8 ml of water are added sequentially. The salts are filtered off and the filtrate is evaporated to yield 6-aminomethyl-3-benzyloxy-2-methylpyridine; NMR: ($CDCl_3$) 1.67 (2H), 2.47 (3H), 3.8 (2H), 4.95 (2H).

A solution of 6-aminomethyl-3-benzyloxy-2-methylpyridine (6.31 g) in 8.7 ml of formic acid is heated at 90° for 15 hours. The reaction mixture is cooled, made basic with ice-cold ammonium hydroxide solution and extracted with chloroform. (3×25 ml). The chloroform extract is dried over sodium sulfate and evaporated. Recrystallization from ether yields 3-benzyloxy-6-formylaminomethyl-2-methylpyridine, m.p. 67°-68°.

A solution of 3-benzyloxy-6-formylaminomethyl-2-methylpyridine (5.14 g) and phosphorus oxychloride (4.0 ml) in 18 ml of toluene is heated at 90° for 15 hours. The solvent is evaporated and the residue taken up in chloroform (50 ml), cooled to 0° and made basic with ice-cold ammonium hydroxide solution. The aqueous phase is further extracted with chloroform (3×20 ml) and the organic phase is dried over sodium sulfate. Evaporation yields an oil (3.84 g) which is passed through 38 g of silica gel with ethyl acetate. Recrystallization of the resulting solid from ether yields 6-benzyloxy-5-methylimidazo-[1,5-a]pyridine, m.p. 52°-54°.

The starting 7-(3-chloropropyl)imidazo[1,5-a]pyridine for compound e is prepared as follows:

Peracetic acid (40%, 5.0 ml) is added to 4-(3-chloropropyl)pyridine (5.18 g) at such a rate as to keep the reaction temperature at 80°. The mixture is stirred until the temperature falls to 30°. Excess peracid is destroyed with sodium sulfite solution and the solvent is vacuum distilled. The residue is redissolved in methylene chloride (50 ml), filtered and evaporated to yield and crude 4-(3-chloropropyl)-pyridine-N-oxide which is heated to 80° in dimethyl sulfate (4.66 g) for 2 hours. The resulting 4-(3-chloropropyl)-1-methoxypyridinium methyl sulfate salt is dissolved in 10 ml of water, cooled to 0° and reacted with an ice-cold solution of potassium cyanide (6.7 g, 100 mmol) in 20 ml of 0.25N sodium hydroxide solution for 22 hours. The product is extracted with methylene chloride (3×30 ml) and dried over sodium sulfate. The solvent is evaporated and the residue filtered through 45 g of silica gel with ether to yield 4-(3-chloropropyl)-2-cyanopyridine; NMR ($CDCl_3$) 3.56 (t, 2H), 7.40 (d, 1H), 7.57 (s, 1H), 8.60 (d, 1H).

A solution of borane-dimethylsulfide (0.83 ml, 7.7 mmol) in 7 ml of tetrahydrofuran is added slowly to a refluxing solution of 4-(3-chloropropyl)-2-cyanopyridine (1.24 g, 6.9 mmol) in 7 ml of tetrahydrofuran while dimethylsulfide simultaneously distills off. The mixture is refluxed for 15 minutes after the addition is complete, cooled to 30° and 6 ml of 6N hydrochloric acid is added. After hydrogen evolution ceases, the mixture is refluxed for 30 minutes, cooled to 0° and saturated with solid sodium carbonate before extracting with methylene chloride (4×50 ml). The organic extracts are dried over sodium sulfate and evaporated to yield an oil which is filtered through 10 g of silica gel (1:1 EtOAc-MeOH) to yield 2-aminomethyl-4-(3-chloropropyl)-pyridine as a yellow oil; NMR (CDCl$_3$) 3.55 (t, 2H), 4.20 (s, 2H).

A solution of 2-aminomethyl-4-(3-chloropropyl)pyridine (0.47 g) in 1 ml of formic acid is heated at 90° for 18 hours, cooled to 0° and made basic by the addition of saturated ammonium hydroxide solution. Extraction with methylene chloride (4×10 ml), drying over sodium sulfate and evaporation yields 2-(N-formylaminomethyl)-4-(3-chloropropyl)pyridine (IR 1674 cm$^{-1}$) which is heated at 90° in phosphorus oxychloride (0.75 g) for 15 hours. Excess phosphorus oxychloride is evaporated with toluene and the residue is suspended in methylene chloride (15 ml), cooled to 0° and made basic with saturated ammonium hydroxide. Extraction with methylene chloride (4×15 ml), drying over sodium sulfate and preparative thin layer chromatography (silica gel, EtOAc) of the residue yields 7-(3-chloropropyl)-imidazo[1,5-a]pyridine (Rf=0.24, EtOAc) as a gum; NMR (CDCl$_3$) 3.58 (t, 2H), 6.42 (q, 1H), 7.21 (s, 1H), 7.32 (s, 1H), 7.88 (d, 1H), 8.07 (s, 1H).

EXAMPLE 30

Preparation of 10,000 tablets each containing 10 mg of active ingredient:

| Formula: | |
|---|---|
| 5-(4-carboxybuta-1,3-dienyl)imidazo[1,5-a]pyridine | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 31

Preparation of 10,000 capsules each containing 25 mg of the active ingredient:

| Formula: | |
|---|---|
| 5-[p-(2-carboxyprop-1-enyl)phenyl]-imidazo[1,5-a]pyridine | 250.0 g |
| Lactose | 1650.0 g |
| Talcum powder | 100.0 g |

PROCEDURE

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Similarly prepared are tablets and capsules comprising about 10–100 mg of other compounds of the invention, e.g. compounds given in the examples herein.

What is claimed is:
1. A compound of the formula

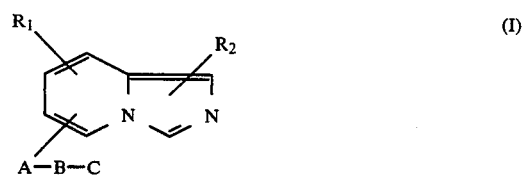

wherein the group -A-B-C is attached at the 5-position of the imidazo[1,5-a]pyridine nucleus or a 5,6,7,8-tetrahydro derivative thereof, wherein R$_1$ is hydrogen, halogen, lower alkyl, lower alkoxy, hydroxy or aryl-lower alkoxy in which aryl represents phenyl or phenyl substituted by lower alkoxy, lower alkyl, halogen or trifluoromethyl; R$_2$ represents hydrogen, halogen, or lower alkyl; C represents carboxy, lower alkoxycarbonyl, unsubstituted or mono- or di-(lower alkyl)substituted carbamoyl, cyano, formyl, hydroxymethyl, 5-tetrazolyl, 4,5-dihydro-2-oxazolyl, 4,5-dihydro-2-oxazolyl substituted by lower alkyl, or hydroxycarbamoyl; and (a) A represents ethenylene or ethenylene substituted by lower alkyl; and B is alkynylene or alkenylene of 2 to 12 carbon atoms each, phenylene-lower alkylene, phenylene-lower alkenylene or phenylene-(thio or oxy)-lower alkylene; or (b) A represents a direct bond; and B represents phenylene-lower alkylene, lower alkylene-(thio or oxy)-lower alkylene, phenylene-(thio or oxy)-lower alkylene, phenylene-lower alkenylene, lower alkylenephenylene-lower alkenylene, or lower alkylene-butadienylene; or a pharmaceutically acceptable salt thereof.

2. A compound according to claim 1 wherein R$_1$ is hydrogen, halogen, lower alkyl, lower alkoxy, hydroxy, phenyl-lower alkoxy, or phenyl-lower alkoxy mono- or di-substituted on the phenyl ring by lower alkoxy, lower alkyl or halogen; R$_2$ represents hydrogen, halogen or lower alkyl; A represents ethenylene or ethenylene substituted by lower alkyl; B is alkynylene or alkenylene of 2 to 12 carbon atoms each, phenylene-lower alkylene, phenylene-lower alkenylene, phenylene-(thio or oxy)-lower alkylene; C represents carboxy, lower alkoxycarbonyl, unsubstituted or mono- or di-(lower alkyl) substituted carbamoyl, cyano, hydroxymethyl, 5-tetrazolyl, 4,5-dihydro-2-oxazolyl, 4,5-dihydro-2-oxazolyl substituted by lower alkyl, hydroxycarbamoyl or formyl; or a pharmaceutically acceptable salt thereof.

3. A compound according to claim 2 wherein A represents ethenylene; B represents alkenylene of 2 to 12 carbon atoms, phenylene-oxy-lower alkylene; R$_1$, R$_2$ and C are as defined in claim 2; or a pharmaceutically acceptable salt thereof.

4. A compound according to claim 2 wherein A represents ethenylene; B represents alkenylene of 2 to 6 carbon atoms each, or phenylene-oxy-alkylene of 7 to 11 carbon atoms; $R_1$ and $R_2$ are hydrogen and C represents carboxy or lower alkoxycarbonyl; or a pharmaceutically acceptable salt thereof.

5. A compound according to claim 2 of the formula

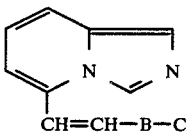

(II)

wherein B represents alkenylene of 2 to 4 carbon atoms; C represents carboxy or lower alkoxycarbonyl; or a pharmaceutically acceptable salt thereof.

6. A compound of the formula

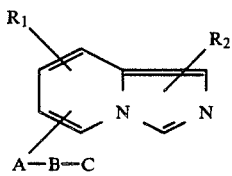

(I)

wherein the group —A—B—C is attached at the 5-position of the imidazo[1,5-a]pyridine nucleus or a 5,6,7,8-tetrahydro derivative thereof, wherein $R_1$ is hydrogen, halogen, lower alkyl, lower alkoxy, hydroxy, or aryl-lower alkoxy in which aryl represents phenyl or phenyl mono- or di-substituted by lower alkoxy, lower alkyl, halogen or trifluoromethyl; $R_2$ represents hydrogen, halogen or lower alkyl; C represents carboxy, lower alkoxycarbonyl, unsubstituted or mono- or di-(lower alkyl) substituted carbamoyl, cyano, hydroxymethyl, formyl, 5-tetrazolyl, 4,5-dihydro-2-oxazolyl, 4,5-dihydro-2-oxazolyl substituted by lower alkyl, or hydroxycarbamoyl; A represents a direct bond; and B represents lower alkylene-phenylene-lower alkylene, phenylene-lower alkylene, lower alkylene-(thio or oxy)-lower alkylene, phenylene-(thio or oxy)-lower alkylene, phenylene-lower alkenylene, lower alkylenephenylene-lower alkenylene, lower alkylene-butadienylene; or a pharmaceutically acceptable salt thereof.

7. A compound according to claim 6 wherein A represents a direct bond; B represents phenylenealkylene of 7 to 10 carbon atoms, lower alkylene-(thio or oxy)-lower alkylene of 4 to 10 carbon atoms, or phenylene-lower alkenylene of 8 to 10 carbon atoms, C represents carboxy, lower alkoxycarbonyl, carbamoyl, hydroxycarbamoyl, 5-tetrazolyl or hydroxymethyl; $R_1$ and $R_2$ are hydrogen; or a pharmaceutically acceptable salt thereof.

8. A compound according to claim 6 of the formula

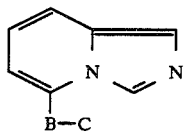

(III)

wherein B represents lower alkylene-(thio or oxy)-lower alkylene of 4 to 10 carbon atoms, phenylene-lower alkylene of 7 to 10 carbon atoms, or phenylene-lower alkenylene of 8 to 10 carbon atoms; C represents carboxy, lower alkoxycarbonyl or carbamoyl; or a pharmaceutically acceptable salt thereof.

9. A compound according to claim 2 being 5-(4-carboxybutadienyl)-imidazo[1,5-a]pyridine or a pharmaceutically acceptable salt thereof.

10. A compound according to claim 6 being 5-[p-(2-carboxyprop-1-enyl)phenyl]-imidazo[1,5-a]pyridine or a pharmaceutically acceptable salt thereof.

11. A compound according to claim 6 being 5-(9-carboxy-nona-6,8-dienyl)-imidazo[1,5-a]pyridine or a pharmaceutically acceptable salt thereof.

12. A pharmaceutical composition suitable for oral or parenteral administration to mammals for the treatment or prevention of diseases responsive to selective inhibition of thromboxane synthetase comprising an effective amount of a compound of claim 1 in combination with one or more pharmaceutically acceptable carriers.

13. A method of selectively inhibiting the release of thromboxane in mammals comprising the administration to said mammal in need thereof of an effective amount of a compound of claim 1.

14. A method of treating diseases responsive to selective thromboxane synthetase inhibition in mammals comprising the administration to a mammal in need thereof of a therapeutically effective amount of a compound of claim 1.

15. A method of treating diseases responsive to selective thromboxane synthetase inhibition in mammals comprising the administration of a therapeutically effective amount of a pharmaceutical composition of claim 12.

16. A method of selectively inhibiting the synthesis of thromboxane for the treatment of cardiovascular and respiratory disorders in a mammal comprising the administration to said mammal in need thereof of a thromboxane synthetase inhibiting pharmaceutical composition suitable for oral or parenteral administration comprising an effective amount of a compound of the formula

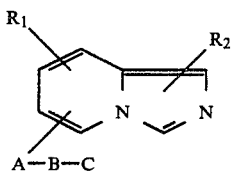

(I)

or a 5,6,7,8-tetrahydro derivative thereof, wherein $R_1$ is hydrogen, halogen, lower alkyl, lower alkoxy, hydroxy or aryl-lower alkoxy in which aryl represents phenyl or phenyl substituted by lower alkoxy, lower alkyl, halogen or trifluoromethyl; $R_2$ represents hydrogen, halogen, or lower alkyl; C represents carboxy, lower alkoxycarbonyl, unsubstituted or mono- or di-(lower alkyl)-substituted carbamoyl, cyano, formyl, hydroxymethyl, 5-tetrazolyl, 4,5-dihydro-2-oxazolyl, 4,5-dihydro-2-oxazolyl substituted by lower alkyl, or hydroxycarbamoyl; and (a) A represents ethenylene or ethenylene substituted by lower alkyl; and B is alkynylene or alkenylene of 2 to 12 carbon atoms each, phenylene-lower alkylene, phenylene-lower alkenylene, phenylene, phenylene-(thio or oxy)-lower alkylene; or (b) A represents a direct bond; and B represents lower alkylenephenylene, phenylene-lower alkylene, phenylene, lower alkylene-(thio or oxy)-lower alkylene, lower alkylene-(thio or oxy)-phenylene, phenylene-(thio or oxy)-lower alkylene, phenylene-lower alkenylene, lower alkylenephenylene-lower alkenylene, or lower alkylene-butadienylene; or a pharmaceutically acceptable salt thereof; in combination with one or more pharmaceutically acceptable carriers.

17. A method according to claim 16 wherein in a compound of formula I the group A—B—C is attached at the 5-position of the imidazo[1,5-a]pyridine nucleus.

18. A pharmaceutical composition suitable for oral or parenteral administration to mammals for the treatment or prevention of diseases responsive to selective inhibition of thromboxane synthetase comprising an effective amount of a compound of claim 6 in combination with one or more pharmaceutically acceptable carriers.

19. A method of selectively inhibiting the release of thromboxane in a mammal comprising the administration to said mammal in need thereof of an effective amount of a compound of claim 6.

20. A method of treating diseases responsive to selective thromboxane synthetase inhibition in mammals comprising the administration to a mammal in need thereof of a therapeutically effective amount of a compound of claim 6.

21. A method of treating diseases responsive to selective thromboxane synthetase inhibition in mammals comprising the administration of a therapeutically effective amount of a pharmaceutical composition of claim 18.

* * * * *